Oct. 18, 1932. J. J. BROOMALL Plant Pat. 36
DAHLIA
Filed June 3, 1932
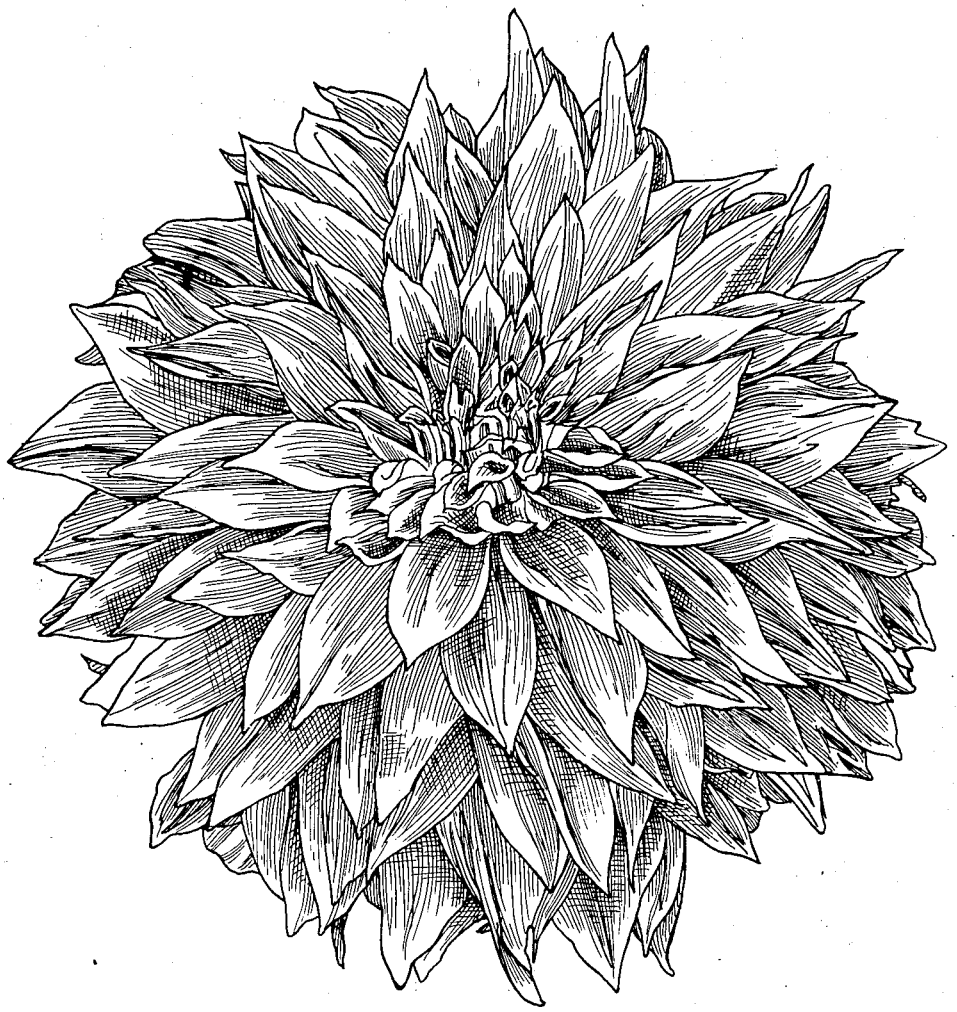
Jesse J. Broomall, INVENTOR
Merlin M. Evans ATTORNEY Patented Oct. 18, 1932

Plant Pat. 36

UNITED STATES PATENT OFFICE

JESSE J. BROOMALL, OF EAGLE ROCK, CALIFORNIA, ASSIGNOR TO CHARLES G. REED, OF LAWRENCE, MASSACHUSETTS

DAHLIA

Application filed June 3, 1932. Serial No. 615,215.

This variety of plant is a dahlia.

In the illustration, the figure is a perspective view of the full bloom of the dahlia.

This is a large pure white decorative dahlia. The bloom is of great depth. The stem holds the mammoth flower erect and upright. The stem is strong. The foliage is resistant to the attacks of insects. The petals of the bloom are devoid of coarseness. The plant is wide branching with tough leather-like foliage that is resistant to insect attacks. The dahlia is a seedling of an informal light pink decorative, a result of years of crossing and recrossing of descendants, resulting from crossing of offspring of *Dahlia juarezii* and *Dahlia variabilis*. The roots of this variety winter well in storage. The bloom of the plant measures sixteen inches in diameter. The plant measures seven feet in height. Foliage is dark green. The color of the matured bloom is pure white and is yellow at the center before all of the petals open.

The dahlia plant is reproduced asexually by division of the individual roots from the clump and planting and growing the roots.

I claim:—

A dahlia as shown and described characterized by its white bloom having distinctive greater dimensions diametrically and axially and all parts of the bloom having relatively proportionate dimensions.

In testimony whereof I affix my signature.

JESSE J. BROOMALL.